United States Patent [19]
Sanders et al.

[11] Patent Number: 5,290,289
[45] Date of Patent: Mar. 1, 1994

[54] NITINOL SPINAL INSTRUMENTATION AND METHOD FOR SURGICALLY TREATING SCOLIOSIS

[76] Inventors: Albert E. Sanders, 7107 Brookside La., San Antonio, Tex. 78209; James O. Sanders, 530 Grandview Pl., Terrell Hills, Tex. 78209; Robert B. More, 1811 Running Brook, Austin, Tex. 78723

[21] Appl. No.: 956,673

[22] Filed: Oct. 5, 1992

Related U.S. Application Data

[63] Continuation-in-part of Ser. No. 526,601, May 22, 1990, abandoned.

[51] Int. Cl.⁵ .............................................. A61B 17/56
[52] U.S. Cl. ..................................... 606/61; 606/151; 623/17
[58] Field of Search .................... 606/61, 151; 623/17

[56] References Cited

U.S. PATENT DOCUMENTS
4,913,386  4/1990  Sugiyama .................. 403/389 X

FOREIGN PATENT DOCUMENTS
0470660  2/1992  European Pat. Off. ............. 606/61

*Primary Examiner*—Randall L. Green
*Assistant Examiner*—D. Willse
*Attorney, Agent, or Firm*—Donald R. Comuzzi

[57] ABSTRACT

A method and implant for the surgical treatment of scoliosis is disclosed. The method involves the segmental fixation of a rigid rod or rods to the abnormally curved portion of the spine. The rod is constructed of a shape-memory alloy such as nitinol. Prior to implementation, the rod is annealed and contoured into an ideal shape for a given patient. At the time of surgery, the rod is deformed to accommodate the existing curvature of the patient's spine and segmentally fixed thereto. The rod is then inductively heated to the transition temperature post-operatively to effect shape recovery and thereby apply corrective forces to the spine.

7 Claims, 1 Drawing Sheet

NITINOL SPINAL INSTRUMENTATION AND METHOD FOR SURGICALLY TREATING SCOLIOSIS

BACKGROUND OF THE INVENTION

This application is a continuation-in-part application of application Ser. No. 07/526,601, filed May 22, 1990, now abandoned.

The present invention relates to an improvement over prior methods and apparatus for surgically treating abnormal curvatures of the spine.

The normal spine possesses some degree of curvature in three different regions. The lumbar spine is normally lordotic (i.e., concave posteriorly), the thoracic spine kyphotic (i.e., convex posteriorly), and the cervical spine also lordotic. These curvatures are necessary for normal physiologic function, and correction is desirable when the spine has either too much or too little curvature in these regions as compared with the norm. A more common abnormality, however, is lateral deviation of the spine or scoliosis.

The first successful internal fixation method for surgically treating scoliosis involves the use of the Harrington instrumentation system. In this method, a rigid rod having hooks at each end is implanted adjacent the concave side of the scoliotic spine. The hooks engage in the facet joints of a vertebra above and under the laminae of a vertebra below the abnormally curved region. At the time of surgery, the spine is manually straightened to a desired extent. The distraction rod is then used to maintain the correction by exerting vertical forces at each end on the two aforementioned vertebra. The rod commonly has a racheted end over which the hooks are slidably mounted and able to be locked in place. The effective length of the rod may thus be adjusted to an appropriate length for exerting the distractive force.

The Harrington distraction rod, because its corrective force is purely distractive, tends to correct curvature in both the frontal and sagittal planes. This means that unwanted loss of normal thoracic kyphosis or lumbar lordosis may inadvertently be produced. To compensate for this, a compression rod is sometimes also used, placed on the convex side of the scoliotic spine. Another variation on the Harrington method which addresses the same problem is to contour the distraction rod in the sagittal plane in accordance with the kyphotic and lordotic curvatures of the normal spine. This may, however, reduce the ability to apply large corrective forces in the frontal plane due to column buckling.

The Harrington instrumentation system has been used successfully but exhibits some major problems. It requires a long post-operative period of external immobilization using a cast or brace. Also, because the distraction rod is fixed to the spine in only two places, failure at either of these two points means that the entire system fails. Failure at the bone-hook interface is usually secondary to mechanical failure of the bone due to excess distractive force.

Another method was thus developed utilizing the concept of segmented fixation. In this method, the spine is manually corrected to a desired degree as before. A rod is then fixed to the spine at multiple points by means of the sublaminar wires (i.e., wires running underneath the lamina of the vertebra and around the rod). The multiple fixation sites add to the stability of the system and make post-operative external immobilization frequently unnecessary. Segmental fixation also makes failure of the entire system much less probable. The possibility that loss of correction will occur post-operatively is also made less likely.

Segmental fixation may be used with a Harrington distraction rod or, as is more usually the case, with a pair of so-called Luque or L-rods. L-rods have a long segment which is aligned with the spine and short segment perpendicular to the long segment. The short segments of the L-rods are inserted in notches or holes made in the spinous processes of vertebra above and below the deformed region of the spine. By placing the two L-rods on opposite sides of the spine and in opposite longitudinal orientation, the entire system is made less vulnerable to vertical migration.

Whether one rod or two is used in the segmental fixation method, the corrective forces are applied in a transverse direction via the sublaminar or spinous process wires rather than in a longitudinal direction as with a Harrington distraction rod. Since the corrective forces as applied transversely, the integrity of the system is not compromised when the rods are contoured to accommodate normal anatomic kyphosis and lordosis.

Another problem with both of the methods described above is their lack of effectiveness in producing rotatory correction in the transverse plane. The longitudinal forces of the Harrington distraction method, with or without an additional compression rod, do not contribute a corrective torque necessary for transverse plane derotation. The segmental fixation method could theoretically apply corrective forces in the transverse plane through the connecting sublaminar wires, but this is dependent on the sequence of wire tightening during implantation and is, as a practical matter, very difficult to achieve. This is unfortunate because scoliosis is generally a three-dimensional deformity requiring some correction in the transverse plane.

The shape-memory alloy, nitinol, has also been attempted as a Harrington rod without segmental fixation to correct scoliosis. This was unsuccessful because the corrective forces could not be transmitted effectively from the rod to the spine.

It is an object of the present invention to provide a method and instrumentation for the surgical treatment of scoliosis using segmental fixation which provides rotatory correction in the transverse plane.

It is a further object of the present invention to provide a method and instrumentation for applying corrective forces to the scoliotic spine while minimizing the forces which must be withstood by the fixation points, thereby lessening the possibility of metal bone interface failure.

It is a still further object of the present method to apply corrective forces to the scoliotic spine in a manner which minimizes the possibility of damage to the spinal cord.

It is a still further object of the present method to allow the easy technical insertion of an implant for correcting scoliosis by deforming the implant to match the shape of the patient's spine.

SUMMARY OF THE INVENTION

The present invention is a method and apparatus which uses a shape memory alloy, such as nitinol, to enhance the function of segmental spine instrumentation in the treatment of scoliotic spinal deformities. Essential to the present invention is that the rod must be segmentally attached to the spine so as to impart transverse and torsional corrective forces to the spine. Furthermore, even though the rod must be affixed to the spine, during some stages of correction it must be free to slide along the spine, while during others it must be rigidly coupled to the spine. Segmental affixation of the rod combined with rod mobility and alternate rod rigidity is accomplished utilizing the bone clamps, which have two designs, and blockers of the present invention both of which are constructed of shape memory material such as nitinol.

The first bone clamp comprises a bone hook having a pincer-type shape formed integrally with a rod housing. During surgery in order to mount the bone clamp to an individual vertebra of the spine, the nitinol bone clamp, which originally is sized to securely fit the vertebrae, is cooled and expanded to a size larger than the vertebra. The bone hook is then placed about the vertebra and heated until it's pincer's snugly encircle the vertebra, thereby, firmly attaching the entire bone clamp to the vertebra. The above process is then repeated until the number of bone clamps necessary to affix the rod to the spine are connected to the bone in all locations.

The second bone clamp comprises two separate members constructed of nitinol which are coupled together during surgery to form the bone clamp. Each member is identical and comprises a claw formed integrally with a rod housing wherein the inner face of the rod housing edge integrally formed with the claw is provided with a hole on one side and a connector rod having a hook at its end on the other. To mount the bone clamp on a vertebra of the spine, the two members are first cooled in order to straighten the hook on the end of each member and expand the claws. The two members are then placed in opposed relation about the vertebra. That is, the claws face each other and surround the vertebra while the connector rod of each member fits through the hole provided in the opposite member. Next, the members are heated which causes the hook at the end of the connector rods to reform, thereby, securing the two members together and preventing their uncoupling. In addition, the claws encircle the vertebra to firmly connect the bone clamp. The above process is then repeated until the number of bone clamps necessary to affix the rod to the spine are connected to the bone in all locations.

To permit the rod to slide along the spine during some stages of correction, yet be held completely rigid during others, the rod housing in the first bone clamp and the two opposed rod housings in the second bone clamp are fitted with a blocker. The blocker comprises a tube constructed of a shape memory material such as nitinol which is circularly-shaped so that the edges the tube overlap. The original shape of the blockers is such that their outer diameters are the same as the correction rod. Additionally, the overlapping shape of the blockers is chosen because it permits their inner diameters to be significantly increased or decreased with only a small concurrent change in their outer diameters. To mount each individual blocker within a rod housing, each blocker is cooled to allow its inner diameter to be expanded and its outer diameter to shrink slightly which permits the blocker to be fit securely within the rod housing while the correction rod easily fits within each blocker. However, although the inner diameters of the blockers are large enough to permit the rod to slide freely, those inner diameters are still small enough to provide a bearing-like fit and surface for the correction rod to the rod housings. That is, the inner surfaces of the blockers contact the correction rod, however, the frictional forces developed between the two surfaces are not sufficient to prevent correction rod movement. When it is necessary to prevent correction rod movement, heat is applied to the blockers, causing them to return to their original shape, thereby completely clamping the correction rod firmly within the rod housing. After the blockers have returned to their original shape, the frictional forces between the inner surfaces of the blockers and the correction rod are sufficient to prevent the rod from sliding.

To practice the present invention, the correction rod is first heated to a temperature at which the crystalline structure of nitinol is entirely in the parent phase. A transformation temperature which is in a 10° C. range of normal body temperature is selected for rod construction. The rod is then contoured to the ideal shape to which it is desired to correct the patient's spine. After that is accomplished, the rod is cooled to the point where the martinsite crystal structure replaces the austenitic phase structure. The rod may now be further deformed but will "remember" the original ideal shape upon being heated to the shape transition temperature.

At the time of surgery, the rod is deformed to a shape which accommodates the existing shape of the patient's scoliotic spine. During this deformation, the temperature of the rod must be maintained below the shape transition temperature. The rod is then segmentally fixed to spine. Some amount of correction may be attained at surgery, but it should be less than the ideal shape to which the rod memory is set so that a potential for shape recovery work exists in the implanted rod. Thus, post-operatively, additional correction may be attained by heating the rod to the shape transition temperature. Because of the segmental fixation, and the fact that the shape recovery of the alloy is a local phenomena, shape recovery forces may be confined to certain vertebral levels as desired by only applying the heat to certain local areas of the rod. Furthermore, the extent of heating, and, thus, the amount of shape recovery force, may be controlled so that the rod moves to its ideal shape to the degree that the spine can withstand without risking neural damage or failure of the metal-bone interface. Also, rotation of the spine due to scoliosis may be corrected by the torque exerted by the rod.

DETAILED DESCRIPTION OF THE INVENTION

Figure 1:
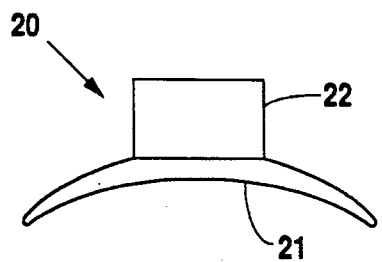
FIG. 1 is a side view showing the first embodiment of the bone clamp of the present invention in the cooled state.

In accordance with the present invention, the implantable rod used to apply corrective forces to the spine is constructed of a shape-memory alloy such as nitinol. Nitinol is a nearly equal atomic ratio of nickel and titanium which exhibits a shape-memory effect. That is, after being deformed (up to about 8% strain) the material remembers its original annealed shape and will return to that original shape when heated above the shape transition temperature. In so doing, the alloy converts heat energy into mechanical work. The mechanical work done while the material is undergoing shape recovery can be much greater than that originally imparted during the initial plastic deformation.

In order for an alloy to exhibit the shape-memory effect, it must be a crystalline structure which can shift into the so-called parent phase when it is subjected to a certain temperature condition and then shift into the configuration known as martensite when the temperature is lowered. The alloy is first annealed to a specified shape. The alloy may then be heated to a temperature high enough that the crystalline structure assumes the parent phase or which is referred to in the art as the austenite configuration. Next, the alloy is cooled until it reverts to the martinsite configuration. The alloy may now be further deformed randomly but will return to the original shape when heated to a temperature above that at which the martinsite returns to the parent phase. The specific transitional temperature at which the phase transition occurs can be controlled by controlling the exact nickel to titanium ratio.

The use of shape-memory alloys for use in the surgical correction of scoliosis has been investigated before, using a Harrington distraction rod constructed of nitinol, but the corrective forces could not be applied effectively to the spine. Several unique advantages occur, however, when the properties of a shape-memory alloy are utilized by a segmental fixation method for correcting scoliosis. These include rotatory correction in the transverse plane, less applied force at the bone-metal interface which increase the efficiency of transverse forces in correcting severely deformed spines in the frontal plane, localized correction applied post-operatively while the patient is monitored to minimize the risk of neural damage, the fact that the rod can be contoured to the pre-operative shape of the patient's spine. The corrective forces can be effectively applied to the spine.

A single rod or a plurality of rods constructed of nitinol is first deformed while in the parent phase crystalline configuration to the ideal shape to which it is desired to eventually correct a particular patient's spine. The rod is then cooled until the martinsite transformation occurs. While maintaining the rod below the shape transition temperature, the rod may be deformed to conform to present shape of the patient's spine, which may include twisting. Alternatively, the rod may deviate somewhat from the spine's preoperative shape in order to apply some correction during surgery. Because all of the corrective potential of the rod is stored as shape-memory, the rod can be positioned to lie immediately adjacent to the spine all along its length. This improves the rigidity of whatever technique of segmental fixation is used because the rod may rest firmly against the spine. In prior methods of segmental fixation, this cannot be accomplished because the rod must necessarily be shaped differently than the patient's preoperative spine. Attempts to approximate such a rod to a lamina by, for example, twisting the wires, risks wire breakage and damage to the patient's spine.

The rod in the present invention is segmentally fixed to the spine using the apparatus and method described herein in order to provide sufficient fixation rigidity and strength. Because, as explained below, the corrective forces are applied gradually in a manner which lessens the stresses borne by the individual fixation points, the present method employs bone clamps (described herein) rather than sublaminar wires to segmentally fix the rod to the spine. The present invention, therefore, by avoiding invasion of the neural canal, greatly reduces the risk of damage to the spinal cord. However, it is to be understood that techniques employing existing devices such as wires, hooks, tape, or screws could be used to secure the correction rod to the scoliotic spine.

Figure 2:
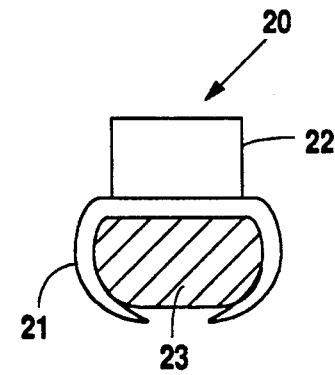
FIG. 2 is a side view showing the first embodiment of the bone clamp of the present invention in the heated state.

Referring to FIGS. 1-2, the first embodiment of the bone clamp according to the present invention will be described. Bone clamp 20 is constructed of nitinol and comprises bone hook 21 having a pincer-type shape formed integrally with rod housing 22. During surgery in order to mount bone clamp 20 to an individual vertebra of the spine, bone clamp 20, which originally is sized to securely fit the vertebrae, is cooled and expanded to a size larger than the vertebra (See FIG. 1). Bone hook 21 is then placed about vertebra 23 and heated until its pincers snugly encircle vertebra 23, thereby firmly attaching bone clamp 20 to vertebra 23 (See FIG. 2). The above process is then repeated until the number of bone clamps necessary to affix the rod to the spine are connected to the bone in all locations.

Figure 3:
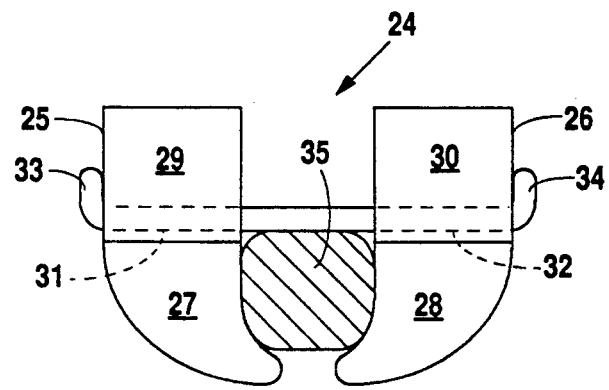
FIG. 3 is a side view showing the second embodiment of the bone clamp of the present invention.
Figure 4:
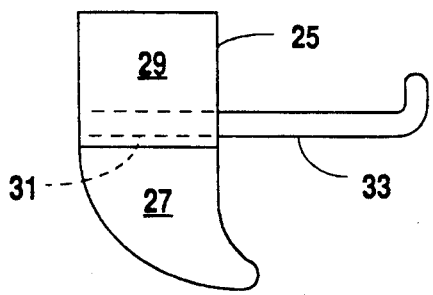
FIG. 4 is a side view showing one member of the bone clamp of the second embodiment of the present invention in the heated state.
Figure 5:
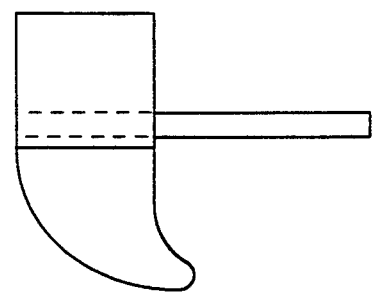
FIG. 5 is a side view showing one member of the bone clamp of the second embodiment of the present invention in the cooled state.

Referring to FIGS. 3-5, the second embodiment of the bone clamp according to the present invention will be described. Bone clamp 24 is constructed of nitinol and comprises first and second members 25 and 26 which are coupled together during surgery to form bone clamp 24 (See FIG. 3). Members 25 and 26 are identical and comprise claws 27,28 formed integrally with rod housings 29,30 wherein the inner face of the rod housing edge integrally formed with claws 27,28 are provided with holes 31,32 on one side and connector rods 33,34 having a hook at its end of the other (See FIG. 4). To mount bone clamp 24 onto vertebra 35 of a spine, first and second members 25 and 26 are cooled in order to straighten the hooks on the end of each member 25,26 and expand claws 27,28 (See. FIG. 5). Members 25,26 are then placed in opposed relation about vertebra 35. That is, claws 27,28 face each other and surround vertebra 35 while connector rods 33,34 of each member 25,25 fit through holes 31,32 provided in the opposite member. Next, members 25,26 are heated which causes the hook at the end of connector rods 33,34 to reform, thereby, securing members 25,26 together and preventing their uncoupling. In addition, claws 27,28 encircle vertebra 35 to firmly connect bone clamp 24. The above process is then repeated until the number of bone clamps necessary to affix the rod to the spine are connected to the bone in all locations.

Although segmental affixation is essential to the present invention so that the correction rod can impart transverse and torsional corrective forces to the spine, it is also essential that the correction rod slide freely along the spine during some stages of correction, while during others it must be rigidly coupled to the spine. To permit the correction rod to slide freely along the spine during some stages of correction, yet be held completely rigid during others, rod housing 22 of bone clamp 20 and rod housings 29,30 of bone clamp 24 are fitted with a blocker.

Figure 6:
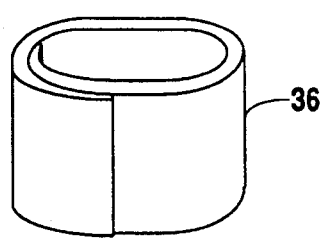
FIG. 6 is a perspective view showing the blocker of both bone clamps of the present invention.
Figure 7:
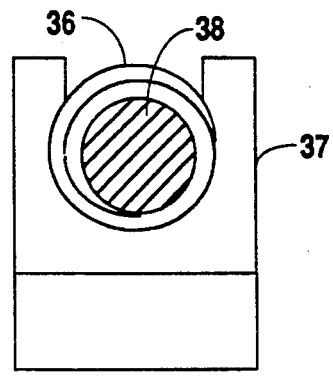
FIG. 7 is a end view showing the mounting of the correction rod within the rod housing of one of the bone clamps of the present invention.

Referring to FIGS. 6 and 7, the blockers, rod housings, and affixation of the correction rod within the housing will be described. Although the affixation of the correction rod to the spine is described with reference to a single rod housing and blocker, it is to be understood that all the blockers and rod housings operate similarly. Blocker 36 is constructed of nitinol and comprises a tube which is circularly-shaped such that its edges overlap (See FIG. 6). The original shape of blocker 36 is such that its outer diameter is the same as the inner diameter of rod housing 37, and its inner diameter is the same as correction rod 38. Additionally, the overlapping shape of blocker 36 is chosen because it permits its inner diameter to be significantly increased or decreased with only a small concurrent change in its outer diameter. To mount blocker 36 within rod housing 37, blocker 36 is cooled to allow its inner diameter to be expanded and its outer diameter to shrink slightly which permits blocker 36 to securely fit within rod housing 37 while correction rod 38 easily fits within blocker 36. However, although the inner diameter of blocker 36 is large enough to permit correction rod 38 to slide freely, that inner diameter is still small enough to provide a bearing-like fit and surface for correction rod 38 to rod housing 37. That is, the inner diameter of blocker 36 is small enough to encircle and contact correction rod 38, but produces insufficient frictional forces to prevent correction rod 38 from sliding. When it is necessary to rigidly secure correction rod 38 to the spine, heat is applied to blocker 36, causing it to return to its original shape, thereby, increasing the frictional forces between blocker 36 and rod 38 sufficiently to clamp correction rod 38 firmly within rod housing 37.

After the correction rod is segmentally fixed to the patient's spine, the surgical operation is complete. Post-operatively, the rod will apply corrective forces to the patient's spine if it is heated above the shape transition temperature and undergoes transformation to the parent phase crystal configuration. The shape-memory effect is a local phenomena. Thus, localized portions of the rod may be heated selectively in order to produce localized correctional forces applied only at selected vertebral levels. Moreover, by controlling the amount of heat transferred to the rod, the corrective forces may be produced gradually in whatever increments the physician deems appropriate This minimizes the stress which must be borne by the fixation points and hence the probability of failure at the bone-metal interface. The incremental application of correctional forces also allows the physician to monitor the patient for any neural dysfunction as the treatment progresses as well as observe the spinal correction actually produced via fluoroscopy.

The preferred method of heating is a radio frequency induction heater. In such a heater, an alternating current is passed through a coil antenna. A time-varying magnetic field is thus produced which induces eddy currents in the metal rod. The eddy currents then produce heat owing to the electrical resistance of the metal. The frequency of the driving current is selected to be low enough to not produce dipole reversals in water molecules and thus avoid any heating of surrounding tissues. This occurs appreciably only when the electromagnetic waves emitted by the antenna are in the microwave region. The preferred frequency, about 450 KH, is well below that.

Although the invention has been described in conjunction with the foregoing, many alternatives, variation and modifications are apparent to those of ordinary skill in the art. Those alternatives, variations and modifications are intended to fall within the spirit and scope of the appended claims.

We claim:

1. A method for surgically correcting a scoliotic spine comprising the steps of:

contouring a rod constructed of a shape-memory alloy to the ideal spinal shape desired for the correction of said scoliotic spine while the crystal structure of said alloy is in the parent phase;

cooling said rod and a plurality of clamps constructed of said shape memory alloy sufficiently so that the crystal structure shifts to the martensite configuration;

deforming said rod to accommodate the existing curvature of said scoliotic spine while maintaining said rod at a temperature below the transition temperature range;

deforming said plurality of clamps while maintaining said clamps at a temperature below the transition temperature range to facilitate their fastening about a plurality of vertebra and their holding of said rod;

segmentally fixing said rod to said scoliotic spine by fastening said rod to said plurality of clamps; and heating said plurality of clamps to impart grasping forces to said plurality of clamps in order to secure said plurality of clamps about said plurality of vertebra and to hold said rod slidably within said clamps;

heating said rod post-operatively so as to impart corrective forces to said scoliotic spine it points where said rod is fastened to said vertebra by said clamps.

2. The method according to claim 1 wherein said fastening of said rod to said clamps is effected through blockers.

3. The method according to claim 2 wherein heating of said rod is accomplished by inducing electrical currents in the alloy with electromagnetic waves at a frequency below that which produces dipole reversals in water molecules.

4. The method according to claim 3 wherein said correction is achieved incrementally by repeated and localized induction of electrical current in said rod.

5. The method according to claim 4 wherein said repeated and localized induction of electrical currents further tightens the hold of said clamps on said rod until said rod is rigidly affixed within said clamps.

6. The method according to claim 1 wherein said shape-memory alloy is nitinol.

7. The method according to claim 1 wherein said rod is rotationally deformed to correspond to the existing rotational abnormality in the scoliotic spine and thereby produces rotational correction when said rod is heated post-operatively.

* * * * *